US00PP37487P2

(12) United States Plant Patent
Jacob Smit

(10) Patent No.: US PP37,487 P2
(45) Date of Patent: Jun. 23, 2026

(54) ***PEPEROMIA* PLANT NAMED 'EC-PEPE-2502'**

(50) Latin Name: *Peperomia caperata*
Varietal Denomination: EC-PEPE-2502

(71) Applicant: Eden Collection B.V., Sappemeer (NL)

(72) Inventor: Obed Jacob Smit, Sappemeer (NL)

(73) Assignee: Eden Collection B.V. (NL)

( * ) Notice: Subject to any disclaimer, the term of this patent is extended or adjusted under 35 U.S.C. 154(b) by 0 days.

(21) Appl. No.: 19/235,742

(22) Filed: Jun. 12, 2025

(51) Int. Cl.
*A01H 5/12* (2018.01)
*A01H 6/00* (2018.01)

(52) U.S. Cl.
USPC ..... Plt./373

(58) Field of Classification Search
USPC ..... Plt./373
CPC ..... A01H 5/12; A01H 5/00; A01H 6/00
See application file for complete search history.

(56) References Cited

PUBLICATIONS

Community Plant Variety Office CPVO Application Consultation Version 4.23.11 retrieved on Sep. 11, 2025 at https://online.plantvarieties.eu/publicConsultationDetails?registerId=20250620&denomination=ec%20pepe%202502, 2 pp. (Year: 2025).*

* cited by examiner

*Primary Examiner* — June Hwu

(57) ABSTRACT

A new and distinct cultivar of *Peperomia* plant named 'EC-PEPE-2502' is disclosed, characterized by rounded. glossy leaves with a unique mosaic pattern of grey to red color, and deep-lying venation. The new cultivar is a *Peperomia*, typically used as an ornamental plant.

3 Drawing Sheets

Figure 1:
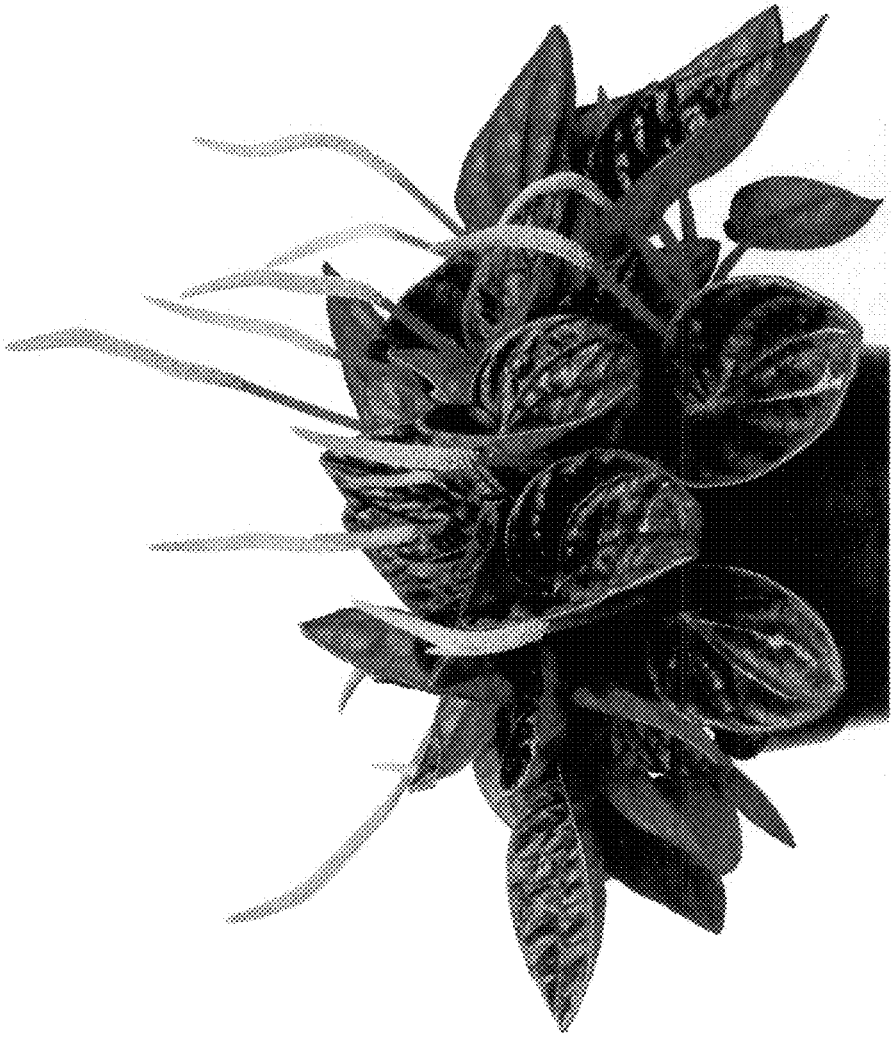

Latin name of the genus and species: *Peperomia caperata.*

Cultivar denomination: 'EC-PEPE-2502'.

BACKGROUND OF THE INVENTION

The new cultivar is the product of a naturally-occurring leaf mutation of *Peperomia caperata* 'EC-PEPE-1904', U.S. Plant Pat. No. 32,564. The new cultivar was found and selected in a commercial greenhouse by the inventor, Obed J. Smit, in Sappemeer, the Netherlands in September 2022.

Asexual reproduction of the new cultivar 'EC-PEPE-2502' by terminal cuttings was first performed in Sappemeer, the Netherlands at a commercial greenhouse in March 2023, and has shown that the unique features of this cultivar are stable and reproduced true to type through successive generations.

SUMMARY OF THE INVENTION

The cultivar 'EC-PEPE-2502' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'EC-PEPE-2502'. These characteristics in combination distinguish 'EC-PEPE-2502' as a new and distinct *Peperomia* cultivar:

1. Round leaves.
2. Unique mosaic pattern of grey and red leaf color.

3. Leaves have deep-lying venation and a shiny, glossy look.
4. Rosette-shaped plant habit.

PARENT COMPARISON

Plants of the new cultivar 'EC-PEPE-2502' are similar to plants of the parent, in most horticultural characteristics, however, plants of the new cultivar 'EC-PEPE-2502' differ in the following characteristics:

1. Leaf color of the new cultivar is a mosaic of grey to red with deep-lying veins, while the leaf color of the parent is grey-green with green, deep-lying veins.
2. Plants of the new cultivar are approximately 30% smaller than plants of the parent.

COMMERCIAL COMPARISONS

Plants of the new cultivar 'EC-PEPE-2502' are similar to plants of the commercial cultivar *Peperomia caperata* 'Eden Rosso', U.S. Plant Pat. No. 24,379. However, plants of the new cultivar differ in the following characteristics:

1. Leaf upper side color of the new cultivar is a mosaic of grey to red with deep-lying veins, while the leaf upper side color of this comparator is dark green.
2. Leaf under side color of the new cultivar is light green, while leaf under side color of this comparator is red.
3. Leaves of the new cultivar are round, while leaves of this comparator are round at the base with a pointed leaf end.

Plants of the new cultivar 'EC-PEPE-2502' are similar to plants of the commercial cultivar *Peperomia caperata* 'Schumi Red', unpatented. However, plants of the new cultivar differ in the following characteristics:

1. Leaf upper side color of the new cultivar is a mosaic of grey to red with deep-lying veins. Leaf upper side color of this comparator is fully red.

2. Leaf under side color of the new cultivar is light green, while leaf under side color of this comparator is red.

BRIEF DESCRIPTION OF THE PHOTOGRAPHS

The accompanying photograph in FIG. 1 illustrates in full color a typical plant of 'EC-PEPE-2502' grown in a greenhouse. The plant is approximately 30 weeks of age.

Figure 2:
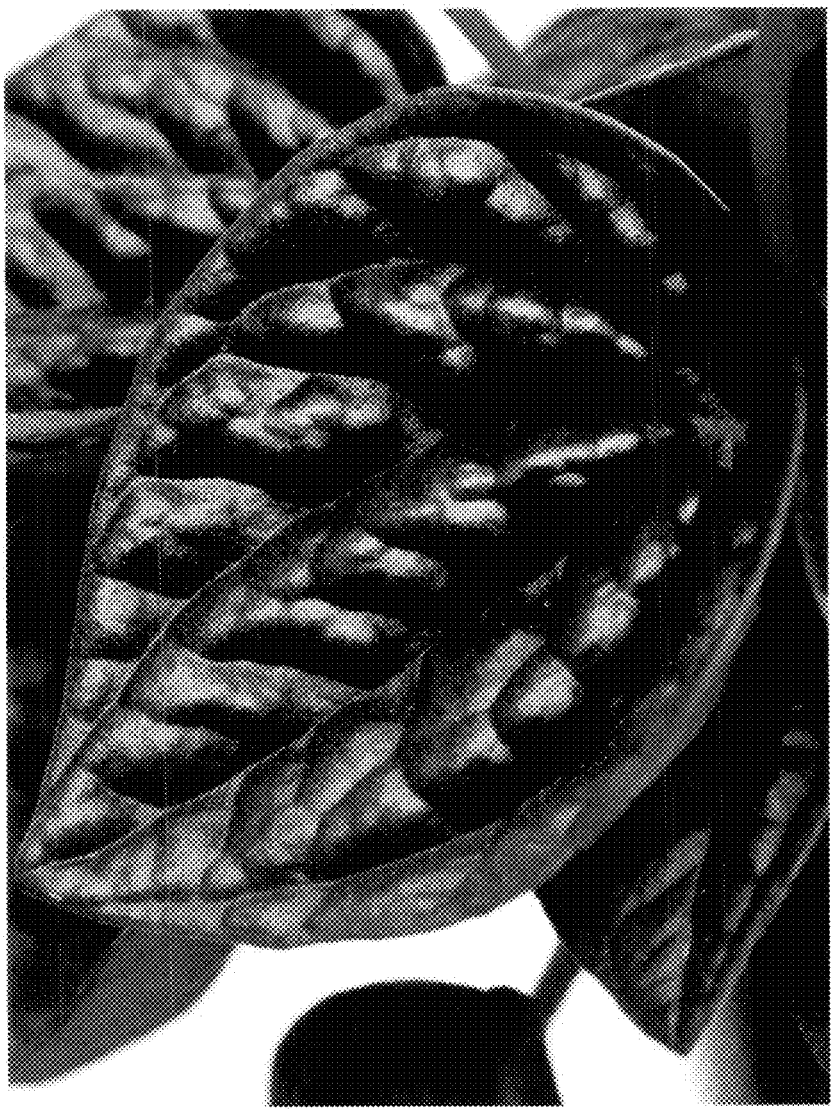
Figure 3:
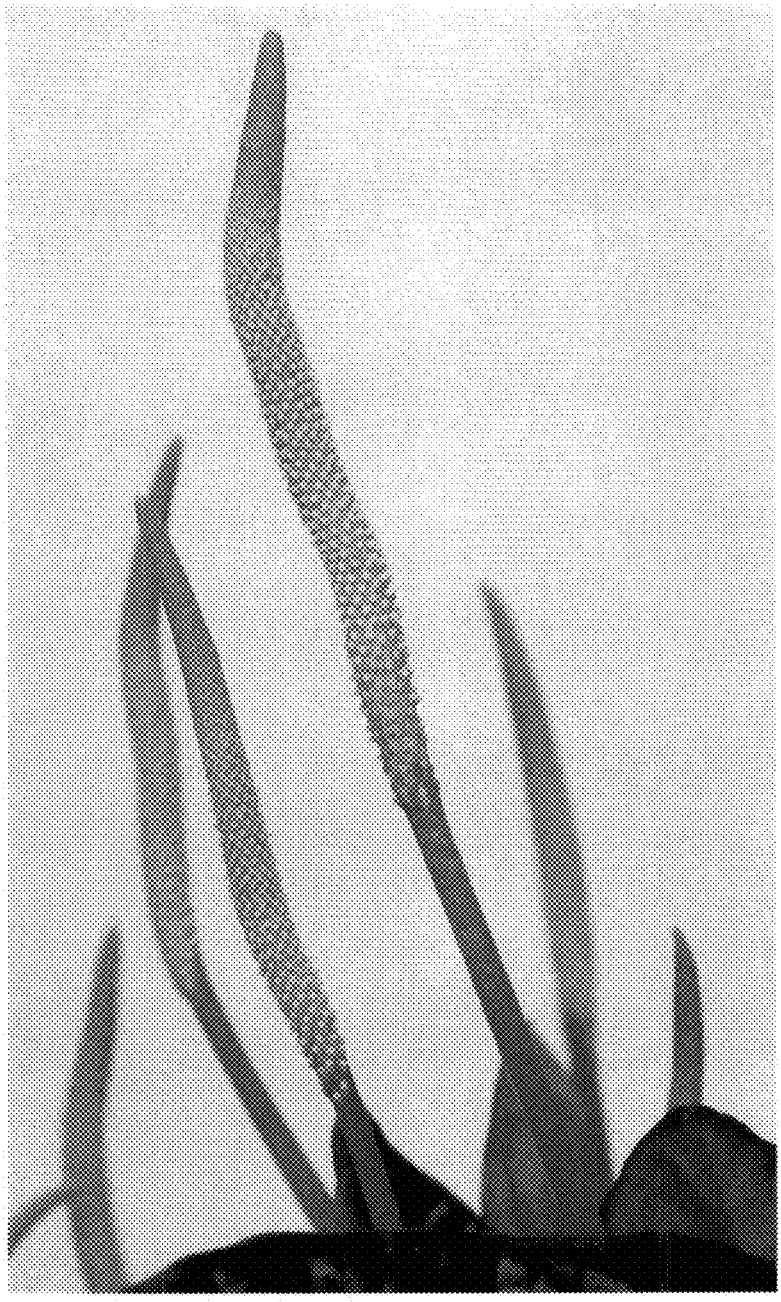

FIG. 2 illustrates a close-up of the foliage.

The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2019 (reprint) except where general terms of ordinary dictionary significance are used. The following observations and measurements describe 'EC-PEPE-2502' plants at 30 weeks of age, grown in a greenhouse in Sappemeer, the Netherlands. The growing temperature ranged from 17° C. to 18° C. at night to 19° C. to 21° C. during the day. Measurements and numerical values represent averages of typical flowering types.

Botanical classification: *Peperomia caperata* 'EC-PEPE-2502'.

PROPAGATION

Time to initiate roots: About 21 days at 21° C. in summer; 28 days at 21° C. in winter.

Time to produce rooted cutting: About 100 days at 21° C. in summer; 120 days at 21° C. in winter.

Description of roots: Herbaceous, fine, moderately dense, freely branching. White in color, not accurately measured with R.H.S. Colour Chart.

PLANT

Plant type: Perennial potted plant.

Plant shape: Flattened to flattened globular.

Growth habit: Rosettes of leaves, eventually forming very short, thick stems.

Plant spread: Approximately 23.7 cm.

Height: 19.9 cm to top of foliar plane; no flowers to date.

Growth rate: Moderate.

Plant vigor: Moderate.

Age of plant described: Approximately 10 months.

Branching habit: Leaves in rosettes, eventually forming very short, thick stems.

Pinching: Pinching not required.

Number of primary (main) branches per plant: Average 6.

Main branches:

*Length*.—Average: 1.5 cm.

*Diameter*.—Average: 0.6 cm.

Internode length: Average: 0.3 cm.

Appearance and shape: Succulent, thick and rounded.

Luster: Matte.

Aspect/angle from vertical: Average angle: 40°.

Strength: Moderately strong.

Color:

*Developing*.—RHS Greyed-Purple 183A.

*Mature*.—RHS Greyed-Purple 187A.

*At internodes*.—RHS Greyed-Purple 187A.

Pubescence: None.

Plant fragrance: None.

FOLIAGE

Leaf:

*Arrangement*.—Alternate, single.

*Quantity*.—Average 23 per plant.

*Average length*.—5.8 cm.

*Average width*.—5.3 cm.

*Shape of blade*.—Orbicular.

*Whole leaf aspect*.—Slightly concave with revolute margin.

*Apex*.—Broad bluntly acute to rounded.

*Base*.—Rounded to shallow truncate, peltate connection of petiole.

*Margin*.—Entire, slightly revolute.

*Texture of top surface*.—Glabrous, smooth, moderately leathery, strongly bullate.

*Texture of bottom surface*.—Glabrous, smooth, moderately leathery.

*Pubescence*.—None.

*Luster, upper side*.—Glossy.

*Luster, under side*.—Very slightly glossy, velvety.

*Rugosity*.—Both sides non-rugose.

*Color*.—Young foliage upper side: RHS Greyed-Green 191C base color with an overcolor of Greyed-Purple 186A flushed with Red 51A and 51B. Young foliage under side: RHS Greyed-Green 193A; veins Greyed-Purple 183A. Mature foliage upper side: RHS Red 53A overcolor. Base color Greyed-Green 192C. The deep red overcolor (53A) begins at the base and intensifies towards the leaf margin. Mature foliage under side: RHS Greyed-Green 193A.

*Venation*.—Pattern: Palmate, strongly furrowed. Venation color upper side: Primary and secondary veins 189A, surrounded by 203D lightly flushed N186A. Venation color under side: RHS Yellow-Green 147B; Greyed-Purple 183A toward the petiole.

*Petiole*.—Average Length: 7 cm. Average Diameter: Upper side of petiole flattened, average diameter at widest (horizontal): 0.33 cm, average diameter at narrowest (vertical): 0.25 cm. Texture: Glabrous, smooth. Luster: Both sides slightly glossy. Strength: Low. Color, upper side: RHS Green 138C; axially striped Greyed-Red 178A; distal end Greyed-Red 178A. Color, under side: RHS Yellow-Green 148C; axially striped Greyed-Red 178B; distal end Greyed-Red 178B.

FLOWER

Not observed to date.

REPRODUCTIVE ORGANS

Not observed.

OTHER CHARACTERISTICS

Seeds and fruits: None observed to date.

Disease/pest resistance: No increased nor decreased resistance nor susceptibility to normal diseases and pests of *Peperomia* has been observed.

Temperature tolerance: Tolerates temperatures up to 40° C. Hardy to USDA zones 10 to 12. Moderate tolerance to rain. High tolerance to wind.

What is claimed is:

1. A new and distinct cultivar of *Peperomia* plant named 'EC-PEPE-2502' as herein illustrated and described.

* * * * *